United States Patent [19]
Bowman et al.

[11] Patent Number: 6,159,458
[45] Date of Patent: Dec. 12, 2000

[54] SUSTAINED RELEASE OPHTHALMIC COMPOSITIONS CONTAINING WATER SOLUBLE MEDICAMENTS

[75] Inventors: Lyle M. Bowman, Pleasanton; James F. Pfeiffer, Oakland, both of Calif.

[73] Assignee: InSite Vision, Alameda, Calif.

[21] Appl. No.: 08/963,815

[22] Filed: Nov. 4, 1997

[51] Int. Cl.[7] .................................................. A61K 31/74
[52] U.S. Cl. ...................... 424/78.04; 514/912; 514/913; 514/914
[58] Field of Search ................................ 424/78.04, 427, 424/428, 484, 486, 487; 514/912, 913, 914, 944, 953, 954, 955

[56] References Cited

U.S. PATENT DOCUMENTS

| | | |
|---|---|---|
| 4,271,143 | 6/1981 | Schoenwald et al. . |
| 4,474,751 | 10/1984 | Haslam et al. . |
| 4,911,920 | 3/1990 | Jani et al. . |
| 5,075,104 | 12/1991 | Gressel et al. . |
| 5,188,826 | 2/1993 | Chandrasekaran et al. . |
| 5,192,535 | 3/1993 | Davis et al. . |
| 5,209,927 | 5/1993 | Gressel et al. . |
| 5,340,572 | 8/1994 | Patel et al. . |
| 5,397,567 | 3/1995 | Löbering et al. . |
| 5,521,168 | 5/1996 | Clark . |

FOREIGN PATENT DOCUMENTS

| | | |
|---|---|---|
| 2 007 091 | 5/1979 | United Kingdom . |
| WO 9200707 | 1/1992 | WIPO . |
| WO 93/17664 | 9/1993 | WIPO . |

OTHER PUBLICATIONS

Thermes er al., "Bioadhesion: The Effect of Polyacrylic Acid on the Ocular Bioavailability of Timolol," *Internantional Journal of Pharmaceutics*, 81:59–65 (1992).

*Primary Examiner*—Carlos Azpuru
*Attorney, Agent, or Firm*—Howrey & Simon

[57] ABSTRACT

An ophthalmic composition that provides sustained release of a water soluble medicament is formed comprising a crosslinked carboxy-containing polymer, a medicament, a sugar and water. The composition has a pH of at least 6.7 but a viscosity of from about 1000 to 5000 cps.

26 Claims, 2 Drawing Sheets

SUSTAINED RELEASE OPHTHALMIC COMPOSITIONS CONTAINING WATER SOLUBLE MEDICAMENTS

BACKGROUND OF THE INVENTION

1. Field of the Invention

The present invention relates to sustained release ophthalmic compositions that contain water soluble medicaments such as timolol and to the pharmacological use thereof.

2. Description of the Related Art

Ophthalmic compositions have been used as drug delivery systems. For example, commonly assigned U.S. Pat. No. 5,192,535 discloses topical ophthalmic medicament delivery systems for sustained release of medicaments. These systems undergo a substantial increase in viscosity upon contact with tear fluid. In one embodiment, the system is an aqueous suspension which comprises about 0.1% to about 6.5%, by weight, of crosslinked carboxyvinyl polymer and has a pH of about 3 to about 6.5. Upon contact with the tear fluid in the eye, which typically has a pH of around 7.2 to 7.4, the pH increases and the polymer expands thereby increasing the viscosity. The resulting more viscous gel remains in the eye for a longer period of time and thus enhances the sustained release of the medicament. Under this system, the initial viscosity (from 1,000 to 30,000 cps) can be low enough so as to facilitate application to the eye in drop form.

U.S. Pat. No. 5,340,572, also commonly owned, discloses topical ophthalmic medicament delivery systems. In one embodiment, the system contains an aqueous suspension of crosslinked carboxyvinyl polymers and a medicament having multiple amine groups (e.g., an antibiotic), at a pH of 7.5 or more. This suspension can be administered in drop form and remains a gel upon contact with tear fluid so as to provide comfortable and sustained release of the medicament. The delivery system preferably has a viscosity in the range of 5,000 to 30,000 cps, although other viscosities are disclosed. The amount of crosslinked carboxyvinyl polymer is typically within the range of from 0.05% to 10%, by weight, based on the total weight of the aqueous suspension.

While the above-mentioned compositions offer excellent properties, it would be beneficial to improve the release profile of medicaments, especially water soluble medicaments, from an ophthalmic composition having a pH of greater than about 6.7 and a viscosity of less than 5000 cps. In this range of relatively high pH and low viscosity, the amount of crosslinked carboxyvinyl polymer that can be present is limited. Greater amounts of the polymer could be added if either the viscosity was permitted to rise or the pH was reduced. By constraining both of these parameters, the amount of polymer that can be added is restricted. Such constraint may at times be acceptable, but the limited amount of polymer can cause a less desirable release profile; namely, the medicament may not be optimally restrained by the polymer and the medicament may be too rapidly released after administration. Such an insufficient restraint is more prevalent with respect to water soluble medicaments.

In contrast, in the case of medicaments that are substantially water insoluble, the medicament must dissolve before it can be readily released from solution. This dissolving step provides a type of delay that can help to provide sustained release. The delay attributable to the dissolution step is not normally present with water soluble medicaments. Thus, improvements in the sustained release of water soluble medicaments from a low viscosity, low polymer content, high pH ophthalmic composition would be desirable.

OBJECTS AND SUMMARY

It is an object of the present invention to provide a novel ophthalmic composition that has a low viscosity and is easily administered in liquid drop form to the eye.

It is another object of the present invention to provide a novel ophthalmic composition that has a pH of greater than about 6.7.

A further object of the invention is to provide a novel ophthalmic composition that provides sustained release of a water soluble medicament.

Another object of the present invention is to provide a novel method for treating diseases by topically applying to eyes a novel ophthalmic composition that exhibits sustained release of a medicament.

Preferred forms of the invention as contemplated accomplish at least some of the above objects. In accordance with the present invention, the release rate profile of a water soluble medicament from an ophthalmic composition having a pH of at least about 6.7 and containing sufficiently low amounts of crosslinked carboxy-containing polymers so as to have a viscosity of from 1000 to 5000 cps, is improved by incorporating a sugar therein. The sugar is preferably mannitol or sorbitol.

One embodiment of the invention is an ophthalmic composition having a pH of at least about 6.7 and a viscosity of from about 1000 to 5000 cps that comprises a pharmacologically effective amount of a water soluble medicament, 0.5% to 2.0% crosslinked carboxy-containing polymer, about 0.5% to 5.0% sugar, and water. Another embodiment relates to a method for treating a disease by topically applying the ophthalmic composition of the present invention to an eye. A preferred embodiment is an ophthalmic composition that comprises (a) water, (b) a polymer component that consists essentially of one or more crosslinked carboxy-containing polymers, (c) sugar and (d) timolol; wherein the composition has a pH of at least 7.0 and a viscosity of from about 1500 to 3500.

This result is surprising in that the prior art uses of sugars have been, in general, as nonionic osomolality enhancing agents. Other uses for sugars and related polyols, as taught in U.S. Pat. Nos. 5,075,104 and 5,209,927, include stabilizing a polymer, such as a carboxyvinyl polymer, in an ophthalmic composition for dry eye/lubricant applications. None of the prior art teaches the use of a sugar as a medicament release profile enhancer.

The polymers suitable for use in the present invention include those described and suggested in U.S. Pat. No. 5,192,535 and U.S. Pat. No. 5,188,826. These polymers are typically comprised of lightly crosslinked polymers of acrylic acid. As used herein "lightly crosslinked" means that the crosslinking agent comprises from 0.01 to 5.0 wt %, based on the total weight of all monomers present in the polymeric product.

DETAILED DESCRIPTION

Figure 1:
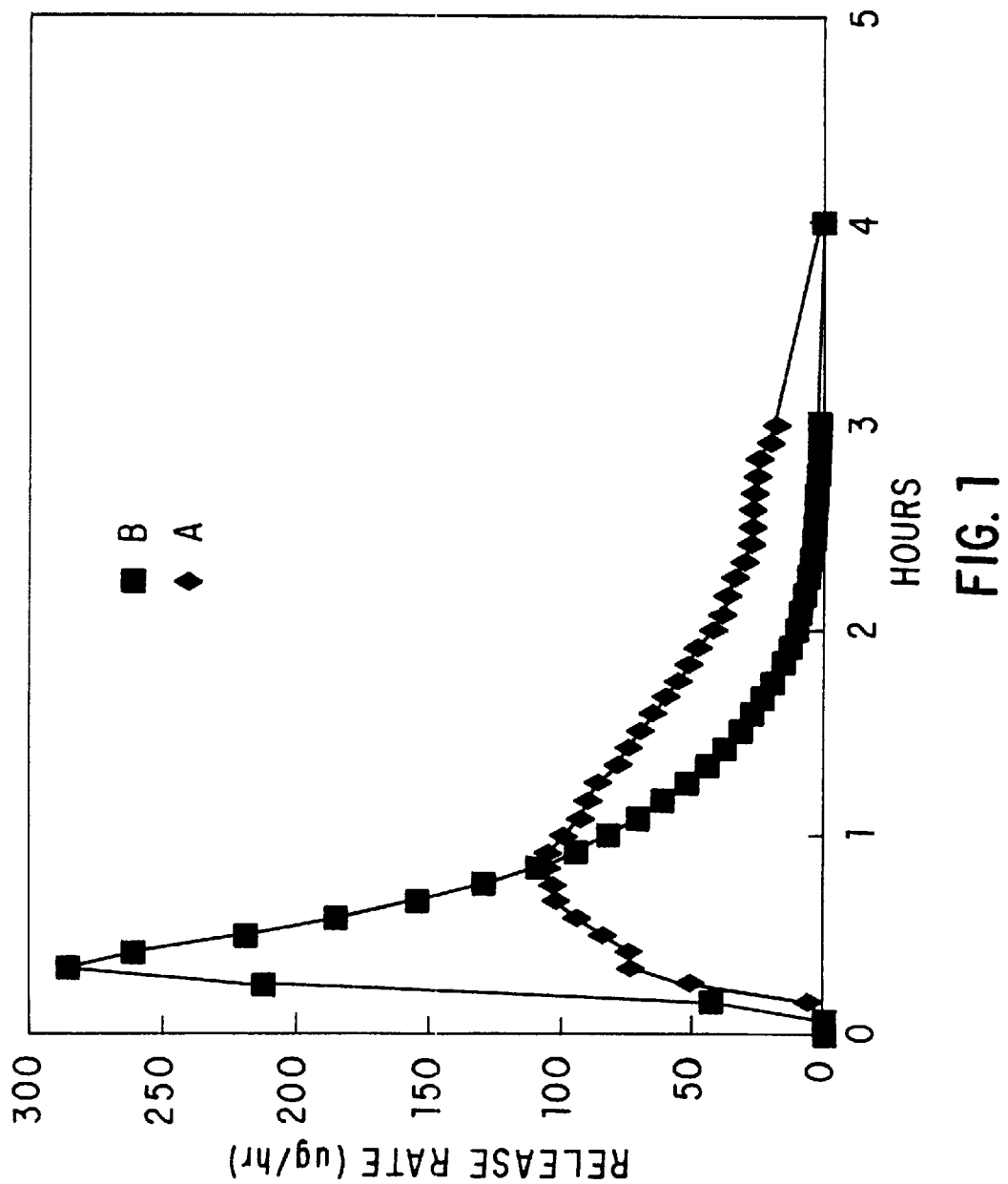
FIG. 1 sets forth the illustrious results of Example 2 regarding low viscosity pair of compositions (A and B).

The ophthalmic compositions of the present invention contain a medicament that is released after application in sustained fashion. Sustained release means that the medicament is released slowly over time so as to provide a longer exposure of the medicament to the eye, which in turn typically increases the bioavailability. A "medicament" means any substance or drug that is useful in treating or ameliorating a disease or medical condition. The disease or medical condition can be in the eye or its surrounding tissue, but is not limited thereto; i.e., treating a condition remote from the eye via topical administration on the eye. The medicament used in the present invention is "water soluble," which means that the medicament has a solubility in water of at least 1 gram per liter of water (0.1%) and typically at least 1.0%.

Examples of water soluble medicaments for use in the present invention include beta blockers such as timolol, levobunolol, betaxolol and atenolol; antibiotics such as tobramycin; anti-inflammatory agents such as ibuprofen; antivirals; and anesthetics. Medicaments include the normal or free base form of the compound as well as the pharmacologically safe salts and the pharmacologically safe esters thereof.

The amount of medicament used in the present invention is an amount effective to treat or ameliorate a disease or medical condition. Generally, the concentration of the medicament will be about 0.001% to about 5.0%, preferably 0.005% to 2.0%, and more preferably from 0.1% to 1.0% based on the weight of the composition. The weight percent in this context refers to the equivalent weight of the active drug (free base form) used; i.e., the weight of an equimolar amount of the free base form of the drug.

Timolol is a preferred medicament and can be used to treat a variety of conditions, including glaucoma. A preferred form is timolol maleate. Preferably, the composition contains from about 0.1% to about 1.0% by weight, more preferably from 0.2% to 0.6%, of timolol. For convenience, the timolol amounts referred to, when timolol maleate or other non-free base form is used, are based on the weight of an equimolar amount of the timolol free base.

The present composition advantageously improves corneal penetration of timolol at high pH levels while also providing a sustained release regime. Corneal penetration, and to a lesser extent conjunctiva penetration, by timolol increases with increasing pH, as indicated in Ashton et al, "Formulation Influence on Conjunctival Penetration of Four Beta Blockers in the Pigmented Rabbit: A Comparison with Corneal Penetration," Pharmaceutical Research, Vol. 8, No. 9, pg 1166–1174, 1991. A pH of 7.4 and 8.4 reportedly showed significant increases in timolol corneal penetration over a pH of 6.4. This is said to be a function of the lipophilicity and pKa of timolol. It is accordingly advantageous to formulate timolol ophthalmic compositions of the present invention at a pH of greater than 7.0.

Generally, one form of the present invention uses a water soluble medicament that is lipophilic and has a log partition coefficient of at least 2.0, preferably 3.0 (using n-octanol/pH 7.4 buffer). In this way, the higher pH of the present invention will allow for better corneal penetration of the medicament. An example of another beta blocker that also meets this partition coefficient parameter is levobunolol, which is preferably used in the form of levobunolol HCl.

Crosslinked carboxy-containing polymers used in practicing this invention are, in general, well known in the art. In a preferred embodiment such polymers may be prepared from at least about 90% and preferably from about 95% to about 99.9% by weight, based on the total weight of monomers present, of one or more carboxy-containing monoethylenically unsaturated monomers. Acrylic acid is the preferred carboxy-containing monoethylenically unsaturated monomer, but other unsaturated, polymerizable carboxy-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers may be crosslinked by a polyfunctional crosslinking agent, preferably a difunctional crosslinking agent. The amount of crosslinking should be sufficient to form insoluble polymer particles, but not so great as to unduly interfere with sustained release of the medicament. Typically the polymers are only lightly crosslinked. Preferably the crosslinking agent is contained in an amount of from about 0.01% to about 5%, preferably from about 0.1% to about 5.0%, and more preferably from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallymethacrylamide and the like. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250.

The crosslinked polymers may be made from a carboxy-containing monomer or monomers as the sole monoethylenically unsaturated monomer present, together with a crosslinking agent or agents. Preferably the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers. Particularly preferred polymers are lightly crosslinked acrylic acid polymers wherein the crosslinking monomer is 2,3-dihydroxyhexa-1,5-diene or 2,3-dimethylhexa-1,5-diene. Preferred commercially available polymers include polycarbophil (Noveon AA-1) and Carbopol®. Most preferably, a carboxy-containing polymer system known by the tradename DuraSite®, containing polycarbophil, which is a sustained release topical ophthalmic delivery system that releases the drug at a controlled rate, is used in the ophthalmic composition of the present invention.

The crosslinked polymers used in practicing this invention are preferably prepared by suspension or emulsion polymerizing the monomers, using conventional free radical polymerization catalysts, to a dry particle size of not more than about 50 μm in equivalent spherical diameter; e.g., to provide dry polymer particles ranging in size from about 1 to about 30 μm, and preferably from about 3 to about 20 μm, in equivalent spherical diameter. Using polymer particles that were obtained by mechanically milling larger polymer particles to this size is preferably avoided. In general, such polymers will have a molecular weight which has been variously reported as being from about 250,000 to about 4,000,000, and from 3,000,000,000 to 4,000,000,000.

In the most preferred embodiment of the invention, the particles of crosslinked polymer are monodisperse, meaning that they have a particle size distribution such that at least 80% of the particles fall within a 10 μm band of major particle size distribution. More preferably, at least 90% and most preferably at least 95%, of the particles fall within a 10 μm band of major particle size distribution. Also, a monodisperse particle size means that there is no more than 20%, preferably no more than 10%, and most preferably no more than 5% particles of a size below 1 μm. The use of a monodispersion of particles will give maximum viscosity and an increased eye residence time of the ophthalmic medicament delivery system for a given particle size. Monodisperse particles having a particle size of 30 μm and below are most preferred. Good particle packing is aided by a narrow particle size distribution.

In one embodiment, the ophthalmic composition comprises a polymer component that consists essentially of one or more of the above-described crosslinked carboxy-containing polymers. This means that no additional polymers are present in the composition that would significantly affect the medicament release profile. Polymers and oligomers used as excipients, carriers, demulcents, or other non-medicament-interactive functions are still included within the composition so long as the medicament release profile is not significantly altered. However, in this embodiment no polymer particles (water insoluble polymers) which materially affect release e.g., a cationic exchange resin) are present in addition to the crosslinked carboxy-containing polymers, and typically no other polymers (soluble or insoluble) of any kind are present in the composition.

The ophthalmic composition of the present invention generally contains the crosslinked carboxy-containing polymer in an amount ranging from 0.5 to 2.0%, preferably from 0.5% to about 1.2%, and more preferably from 0.6 to 0.9%, based on the weight of the composition. Although referred to in the singular, it should be understood that one or more species of crosslinked carboxy-containing polymer can be used with the total amount falling within the stated ranges. In one preferred embodiment, the composition contains 0.6 to 0.8 % of a polycarbophil such as NOVEON AA. The crosslinked carboxy-containing polymers are water insoluble and water swellable particles. Because the pH of the composition is at least about 6.7, the polymers are in a swelled state such that further increases in pH upon administration to the eye do not substantially increase the viscosity of the composition. Although the polymer is swelled, the composition is typically best described as a viscous liquid or viscous suspension rather than as a gel.

The sugar used in this invention is a compound made of carbon, hydrogen, and oxygen and has at least four hydroxy groups (OH). Preferably the sugar is a five or six carbon sugar such as mannitol, sorbitol, glucose, sucrose, fructose, and lactose. Most preferred is the use of mannitol or sorbitol. One or a combination of sugar species can be used in the ophthalmic composition of the present invention. The total amount of all sugar species contained in the composition ranges from about 0.5% to 5.0%, more preferably 0.5% to 2.0%, by weight, based on the total weight of the composition.

The ophthalmic composition has a viscosity of from 1000 to 5000 cps, measured at a shear rate of 2.25 $\sec^{-1}$ using a Brookfield Digital LV-CP viscometer equipped with a CP-40 spindle at 25° C. At viscosities greater than 5000 cps, the handling and administration of the composition via an eye dropper can become unnecessarily cumbersome and error prone. At viscosities less than 1000 cps, the composition may be too easily washed from the eye by tearing and the like and may not have enough residence time in the eye. Also, because the viscosity is predominantly a function of the kind and amount of crosslinked carboxy-containing polymer (as a function of pH), the amount of crosslinked carboxy-containing polymer present at such a low viscosity is generally too low to provide the desired release profile of medicament. In view of these competing interests, a preferred viscosity range is from 1500 to 3500, more preferably from 2000 to 3000 cps.

The pH of the ophthalmic composition is at least about 6.7. The composition does not substantially change viscosity after administration to the eye as do the compositions described in U.S. Pat. No. 5,192,535. Typically the pH of the composition will not be above 9.0, more preferably not above 8.5, in view of the physiology of the eye. However, with regard to medicaments that exhibit a log partition coefficient value of at least 2.0, a higher pH permits greater penetration and thus greater bioavailability. From this point of view, a pH towards 8.0 or higher is desirable. In balancing a variety of factors overall, a preferred pH is from 7.0 to 7.8, more preferably about 7.4.

As mentioned above, the ophthalmic compositions of the present invention exhibit sustained release of medicament that is comparable to compositions of much higher viscosity and polymer content, even though the viscosity and crosslinked carboxy-containing polymer content are lower. Preferably the compositions of the present invention exhibit a medicament release profile such that no more than 60%, more preferably no more than 50%, of the medicament is released during the first hour after administration. Furthermore, it is preferred that no more than 90%, more preferably no more than 80%, of the medicament is released during the first two hours after administration. These release rates are typically measured in vitro under conditions that model the eye and while frequently the same as or correlated to the in vivo release rate, they are not necessarily synonymous therewith.

For purposes of this application, an ophthalmic composition is considered to meet the above recited release percentages if the percentages are achieved in either an in vitro or an in vivo test. One in vitro test comprises supplying the ophthalmic composition to a release cell that contains a buffer solution at a pH of around 7.4 and that is maintained at a temperature of approximately 37° C. (body temperature). Buffer is steadily passed through the release cell at an appropriate rate to model natural liquid turnover in the eye and is typically approximately ten times the volume of the release cell per hour. The concentration of the medicament in the eluted buffer is measured over time by suitable means, such as spectroscopy, to thereby form a release rate curve. An in vivo test can be carried out using rabbits by procedures well known in the art, such as the one mentioned in Ashton et al., supra.

Ophthalmic compositions according to the present invention typically have a peak release of medicament no sooner than 30 minutes (i.e., peak release occurs at 30 minutes or later), preferably no sooner than 45 minutes, after administration. For comparison purposes, a typical medicated eye drop that does not provide sustained release will exhibit a peak release within 15 minutes after administration in vitro.

The aqueous medium used in the present invention is made of water which has no physiologically or ophthalmologically harmful constituents. Typically purified or deionized water is used. The pH is adjusted by adding any physiologically and ophthalmologically acceptable pH adjusting acids, bases or buffers. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers would include citrate/dextrose, sodium bicarbonate, ammonium chloride and mixtures of the aforementioned acids and bases.

The osmotic pressure ($\pi$) of the present composition is generally from about 10 milliosmolar (mOsM) to about 400 mOsM, more preferably from 260 to 340 mOsM. If necessary, the osmotic pressure can be adjusted by using appropriate amounts of physiologically and ophthalmologically acceptable salts or excipients. Sodium chloride is preferred to approximate physiologic fluid, and amounts of sodium chloride ranging from about 0.01% to about 1% by weight, and preferably from about 0.05% to about 0.45% by weight, based on the total weight of the composition, are typically used. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated range. Furthermore, the need to add a salt or other osmolality adjusting agent may be reduced in view of the presence of a sugar since mannitol, dextrose, sorbitol, glucose and the like also adjust osmolality. Of course more than one sugar can be present in the composition so long as the total amount does not exceed 5.0%.

The composition of the present invention may contain water soluble polymers or water insoluble polymers as a viscosity modifiers or agents. Examples of such soluble polymers are dextran, polyethylene glycols, polyvinylpyrolidone, polysaccharide gels, Gelrite®, and cellulosic polymers like hydroxypropyl methylcellulose as well as other polymeric demulcents. Water insoluble polymers are preferably only crosslinked carboxy-vinyl polymers as discussed above.

The composition of the present invention will ordinarily contain surfactants and, if desired, adjuvants, including additional medicaments, buffers, antioxidants, tonicity adjusters, preservatives, thickeners or viscosity modifiers, and the like. Additives in the formulation may desirably include 0.25% to 0.65% sodium chloride, 0.01% to 0.25% EDTA (disodium edetate), and/or 0.005% to 0.025%, more preferably 0.005% to 0.01% of one or more of the following preservatives: BAK (benzalkonium chloride), sorbic acid, methyl paraben, propyl paraben, and chlorhexidine.

The compositions of the present invention can be prepared from known materials through the application of known techniques by workers of ordinary skill in the art without undue experimentation. In general, compositions are formed by dissolving the desired amount of medicament into water and then combining the crosslinked carboxy-containing polymer therewith. Typically the polymer is combined and mixed so as to form an aqueous suspension of the polymer. The resulting composition is sterilized (e.g., heat sterilized) and then the remaining ingredients such as buffers, surfactants, etc. are added thereto. Alternatively, the medicament or an aqueous solution thereof, can be combined with a sterilized aqueous polymer dispersion, optionally containing buffer, surfactant, and/or other ingredients.

The ophthalmic compositions according to the present invention can be topically administered to the eye in accordance with techniques well known to persons skilled in the art. The ophthalmic composition is preferably administered via a conventional bulb-actuated eye dropper. The finished formulations are preferably stored prior to use in opaque or brown containers to protect them from light exposure, and under an inert atmosphere. These compositions can be packaged in preservative-free single-dose non-reclosable containers. This permits a single dose of the medicament to be delivered to the eye as a drop, with the container then being discarded after use. Such containers minimize the potential for preservative-related irritation and sensitization of the corneal epithelium, as has been observed to occur particularly from ophthalmic medicaments containing mercurial preservatives. Multiple dose containers can also be used, if desired, particularly since relatively low viscosities can be obtained in compositions of the invention which permit constant, accurate dosages to be administered dropwise to the eye as many times each day as necessary. In those compositions where preservatives are to be included, suitable preservatives are chlorobutanol, polyquat, benzalkonium chloride, cetyl bromide, sorbic acid, methyl paraben, propyl paraben, chlorhexidine and the like.

All of the above-mentioned U.S. patents as well as the Ashton et al article are each hereby incorporated by reference, in their respective entireties, into the present application. Furthermore, all of the percentages recited refer to weight percent, unless otherwise indicated. The following non-limiting examples serve to illustrate certain features of the present invention.

EXAMPLE 1

A composition is formed from the ingredients shown in the following table in amounts within the stated range. The composition exhibits good sustained release of timolol and has a viscosity of from 1500 to 3500 cps @ 2.25 sec$^{-1}$ under the conditions described above.

| Ingredients | Amount of Each Component Added to make the Formulation Wt. % |
|---|---|
| polycarbophil, U.S.P. | 0.6 to 0.8 |
| edetate disodium, U.S.P. | 0.09 to 0.11 |
| sodium chloride, U.S.P. | 0.25 to 0.45 |
| timolol Maleate, U.S.P. | 0.612 to 0.748 |
| sodium hydroxide, N.F. | q.s to pH 7.0 to 7.8 |

-continued

| Amount of Each Component Added to make the Formulation | |
|---|---|
| Ingredients | Wt. % |
| sorbitol, N.F. | 1.5 |
| glycerin, U.S.P. | 0.2 |
| benzalkonium chloride, N.F. | 0.008 |
| purified water | q.s to 100 |

EXAMPLE 2

To demonstrate the surprising effect of the present invention, two pairs of ophthalmic compositions are prepared: one pair having a viscosity of greater than 10000 cps and one pair having a viscosity of about 2500 cps. In each pair, one of the compositions contains sorbitol while the other does not. The compositions are described below in the following tables.

| Low Viscosity Compositions (≈2500 cps) | | |
|---|---|---|
| Ingredients | A - With Sorbitol (wt %) | B - Without Sorbitol (wt %) |
| polycarbophil | 0.675 | 0.75 |
| EDTA | 0.1 | 0.1 |
| glycerin | 0.2 | 0.2 |
| sodium chloride | 0.35 | 0.6 |
| timolol maleate | 0.68 | 0.68 |
| sorbitol | 1.5 | none |
| sodium hydroxide | 5.46 | 5.65 |
| purified water | 91.71 | 92.77 |

| High Viscosity Compositions (>10,000 cps) | | |
|---|---|---|
| Ingredients | C - With Sorbitol (wt %) | D - Without Sorbitol (wt %) |
| polycarbophil | 1.1 | 1.2 |
| EDTA | 0.1 | 0.1 |
| sodium chloride | 0.4 | 0.57 |
| timolol maleate | 0.68 | 0.68 |
| sorbitol | 1.5 | none |
| sodium hydroxide | 7.9 | 8.62 |
| purified water | 88.32 | 88.83 |

It should be noted that in removing the sorbitol, additional sodium chloride is added in order to maintain the same osmolality between the pairs. Further, samples A and B have significantly less polycarbophil than samples C and D and thereby have a lower viscosity.

Figure 2:
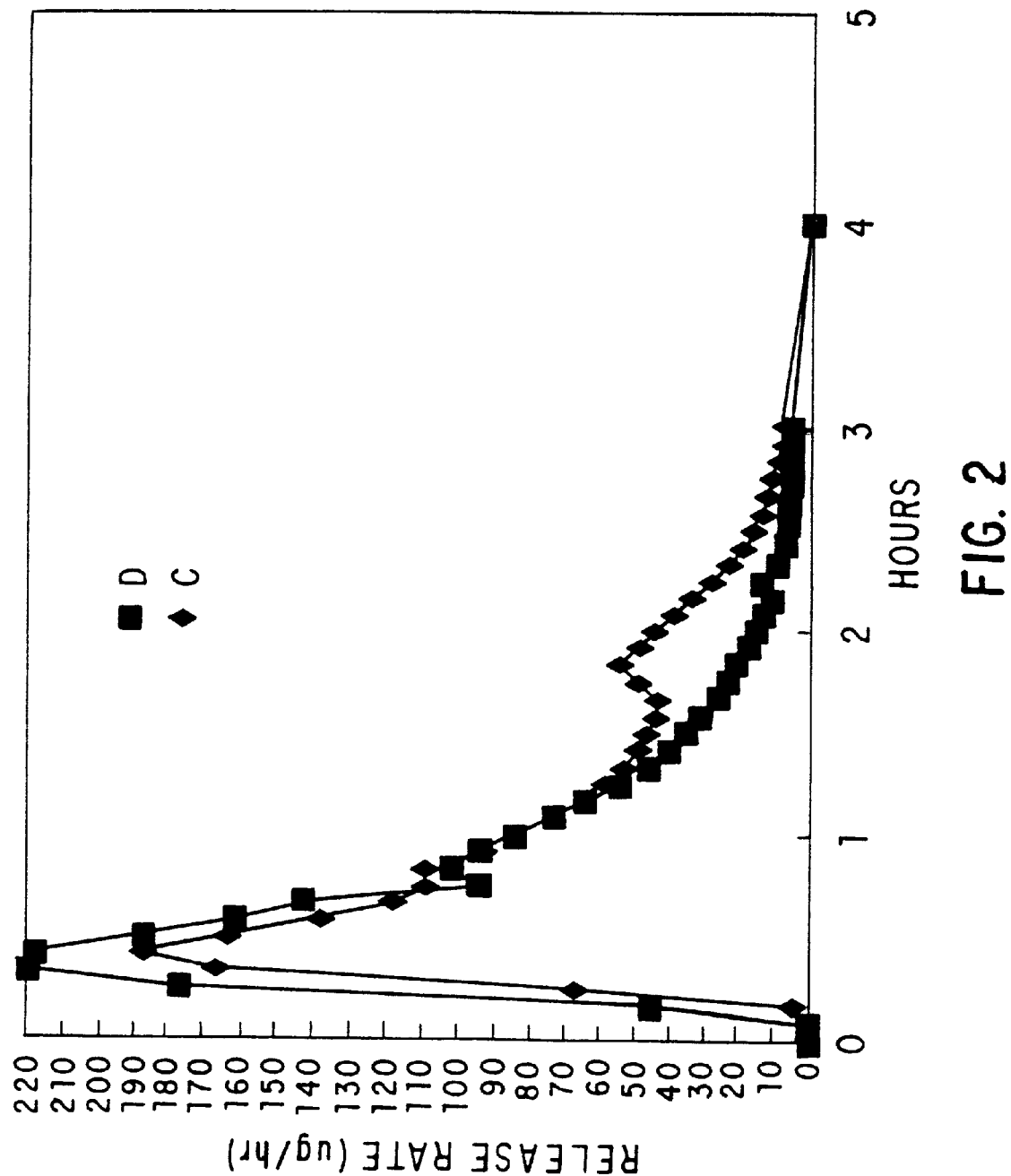
FIG. 2 sets forth the illustrious results of Example 2 regarding high viscosity pair of compositions (C and D).

Each sample is tested in vitro to determine its release rate curve using a cell size of 0.6 ml and a buffer flow rate, via peristaltic pump, of 6 ml/hr. The buffer is a phosphonate buffered saline solution containing 0.9% NaCl and 10 mM phosphate at pH 7.4. Illustrious results are depicted in FIGS. 1 and 2. FIG. 2 shows that the presence or absence of sorbitol has little effect on the release profile in a high viscosity environment. In contrast, FIG. 1 shows that the presence of sorbitol significantly affects the release profile. Indeed, sample B, containing no sorbitol, is essentially not a sustained release composition while sample A, containing sorbitol, exhibits sustained release that is superior to the more viscous/higher polymer content samples C and D. Such a result is surprising.

The above discussion of this invention is directed primarily to preferred embodiments and practices thereof. It will be readily apparent to those skilled in the art that further changes and modifications in actual implementation of the concepts described herein can easily be made or may be learned by practice of the invention, without departing from the spirit and scope of the invention as defined by the following claims.

We claim:

1. An ophthalmic composition comprising:
   a pharmacologically effective amount of a water soluble ophthalmic medicament, about 0.5 to 2.0% crosslinked carboxy-containing polymer, about 0.5 to 5.0% sugar, and water; said composition having a pH of at least about 6.7 and a viscosity of from about 1000 to 5000 cps.

2. The composition according to claim 1, wherein said crosslinked carboxy-containing polymer comprises 0.6% to 0.9% of the composition.

3. The composition according to claim 1, wherein said polymer is a lightly crosslinked carboxy-containing polymer.

4. The composition according to claim 1, wherein the polymer is comprised of at least 90% acrylic acid monomers and 0.1% to 5% crosslinking agent.

5. The composition according to claim 4, wherein the crosslinking agent is a difunctional crosslinking agent.

6. The composition according to claim 4, wherein said crosslinking agent is selected from the group consisting of divinyl glycol, 2,3-dihydroxyhexa-1,5-diene, 2,5-dimethyl-1,5-hexadiene, divinylbenzene; N,N-diallylacrylamide, N,N-diallymethacrylamide, and mixtures thereof.

7. The composition according to claim 1, wherein said polymer is a polycarbophil.

8. The composition according to claim 1, wherein said polymer has a monodisperse particle size distribution.

9. The composition according to claim 1, wherein said medicament has a log partition coefficient value of 2.0 or greater.

10. The composition according to claim 9, wherein said medicament is a beta-blocker.

11. The composition according to claim 10, wherein said medicament is timolol or levobunolol.

12. The composition according to claim 10, wherein said medicament is contained in an amount of from about 0.005% to about 2.0% of said composition.

13. The composition according to claim 12, wherein medicament comprises 0.1% to 1.0% of said composition.

14. The composition according to claim 13, wherein said medicament is timolol maleate or levobunolol HCl.

15. The composition according to claim 1, further comprising EDTA.

16. The composition according to claim 15, wherein said EDTA comprises 0.09% to 0.11% of the composition.

17. The composition according to claim 1, further comprising benzalkonium chloride.

18. The composition according to claim 17, wherein said benzalkonium chloride comprises 0.005% to 0.015% of said composition.

19. The composition according to claim 1, wherein said pH is within the range of from 7.0 to 7.8.

20. The composition according to claim 1, wherein said composition has an osmolality of from 260 to 340 mOsM.

21. The composition according to claim 1, wherein said composition exhibits a medicament release profile such that no more than 60% of said medicament is released during the first hour after administration.

22. A method for treating an eye, which comprises administering to an eye in need thereof an effective amount of the composition according to claim 1.

23. An ophthalmic composition comprising:
(a) water, (b) a polymer component that consists essentially of one or more crosslinked carboxy-containing polymers, (c) sugar, and (c) timolol; wherein said composition has a pH of at least 7.0 and a viscosity of from about 1500 to 3500 cps.

24. The ophthalmic composition according to claim 23, wherein said timolol is present in the form of timolol maleate and in an amount of from 0.2% to 0.6% and wherein said pH is from 7.0 to 7.8.

25. The ophthalmic composition according to claim 23, wherein said composition exhibits a peak release of timolol no sooner than 30 minutes after administration of the composition.

26. The ophthalmic composition according to claim 25, wherein said peak release of timolol occurs 45 minutes or more after administration.

* * * * *